(12) United States Patent
Baker et al.

(10) Patent No.: US 12,154,453 B2
(45) Date of Patent: *Nov. 26, 2024

(54) MEDICAMENT TRAINING DEVICE AND SYSTEM

(71) Applicant: NOBLE INTERNATIONAL, LLC, Orlando, FL (US)

(72) Inventors: Jeff Baker, Orlando, FL (US); Jeffery A. Lettman, Orlando, FL (US); Joshua Hopkins, Casselberry, FL (US); Jaysun Stockdell-Giesler, Oviedo, FL (US); Nicole Weill, Ocoee, FL (US)

(73) Assignee: NOBLE INTERNATIONAL, LLC, Orlando, FL (US)

( * ) Notice: Subject to any disclaimer, the term of this patent is extended or adjusted under 35 U.S.C. 154(b) by 1012 days.

This patent is subject to a terminal disclaimer.

(21) Appl. No.: 17/063,575

(22) Filed: Oct. 5, 2020

(65) Prior Publication Data

US 2021/0090466 A1 Mar. 25, 2021

Related U.S. Application Data

(63) Continuation-in-part of application No. 15/516,581, filed as application No. PCT/US2015/053992 on Oct.
(Continued)

(51) Int. Cl.
*G09B 23/28* (2006.01)
*A61M 5/315* (2006.01)
(Continued)

(52) U.S. Cl.
CPC ....... *G09B 23/285* (2013.01); *A61M 5/31528* (2013.01); *A61M 5/5086* (2013.01); *G16H 20/17* (2018.01); *A61M 2205/50* (2013.01)

(58) Field of Classification Search
CPC .. G09B 23/285; G09B 19/00; A61M 5/31528; A61M 5/5086; A61M 2205/50;
(Continued)

(56) References Cited

U.S. PATENT DOCUMENTS 5,334,173 A 8/1994 Armstrong, Jr.
6,332,875 B2 12/2001 Inkpen et al.
(Continued)

FOREIGN PATENT DOCUMENTS

GB 2515032 A 12/2014
WO 199010470 9/1990
(Continued)

OTHER PUBLICATIONS

EESR for EP 16835945.3; Feb. 12, 2019, 7 pages.
(Continued)

*Primary Examiner* — Amber R Stiles
(74) *Attorney, Agent, or Firm* — Timothy H. Van Dyke; Wolter, Van Dyke, Davis, PLLC

(57) ABSTRACT

In one non-limiting embodiment, there is provided a collateral device for use with one or more medicament devices including a collateral device housing and an opening extending there between, the opening configured to receive an adapter, at least a first sensor associated with the collateral device housing for detecting receipt of the portion of one or more medicament devices into the opening, and detecting actuation of an actuation mechanism of the medicament device; and an adapter receivable within the opening, the adapter comprising a receptacle for receiving and guiding a portion of a medicament device to a target surface.

21 Claims, 2 Drawing Sheets

Related U.S. Application Data 5, 2015, now Pat. No. 10,795,973, which is a continuation-in-part of application No. 14/505,935, filed on Oct. 3, 2014, now Pat. No. 9,767,708.

(51) Int. Cl.
 *A61M 5/50* (2006.01)
 *G16H 20/17* (2018.01)

(58) Field of Classification Search
 CPC .. A61M 2205/3561; A61M 2205/3569; A61M 2205/581; A61M 2209/088; A61M 5/20; A61M 2005/2006; A61M 2005/2013; G16H 20/17; G16H 40/63
 See application file for complete search history.

(56) References Cited

U.S. PATENT DOCUMENTS

| | | | |
|---|---|---|---|
| 6,877,658 B2 | 4/2005 | Raistrick et al. | |
| 6,997,906 B2 | 2/2006 | Langley et al. | |
| 7,367,502 B2 | 5/2008 | Raistrick | |
| 8,172,082 B2 | 5/2012 | Edwards et al. | |
| 8,622,973 B2 | 1/2014 | Edwards et al. | |
| 10,795,973 B2 * | 10/2020 | Baker | G09B 19/0053 |
| 2002/0133114 A1 * | 9/2002 | Itoh | A61P 19/08 |
| | | | 604/122 |
| 2002/0165491 A1 | 11/2002 | Reilly | |
| 2003/0163287 A1 | 8/2003 | Vock et al. | |
| 2003/0229308 A1 | 12/2003 | Tsals et al. | |
| 2005/0182358 A1 | 8/2005 | Veit et al. | |
| 2005/0197650 A1 * | 9/2005 | Sugimoto | A61M 5/31541 |
| | | | 604/890.1 |
| 2008/0059133 A1 | 3/2008 | Edwards et al. | |
| 2009/0212475 A1 | 8/2009 | Tropf | |
| 2012/0008811 A1 | 1/2012 | Edwards et al. | |
| 2013/0245545 A1 * | 9/2013 | Arnold | A61M 5/1723 |
| | | | 604/66 |
| 2013/0266919 A1 | 10/2013 | Baker et al. | |
| 2014/0276550 A1 | 9/2014 | Uram et al. | |
| 2015/0088092 A1 | 3/2015 | Holm et al. | |
| 2023/0377483 A1 * | 11/2023 | Baker | G09B 23/285 |

FOREIGN PATENT DOCUMENTS

| | | |
|---|---|---|
| WO | 2011117212 A1 | 9/2011 |
| WO | 2013120775 A1 | 8/2013 |
| WO | 2013120776 A1 | 8/2013 |
| WO | 2013120777 A1 | 8/2013 |
| WO | 2013160333 A2 | 10/2013 |
| WO | 2014145535 A3 | 9/2014 |
| WO | 2014164948 A1 | 10/2014 |
| WO | 2015052519 A1 | 4/2015 |
| WO | 2016054634 A1 | 4/2016 |

OTHER PUBLICATIONS

Baker, Jeff; "Educating patients on self-administered drug injections", Pharmaceutical Commerce, Jan. 20, 2014, 3 pages.

PCT search report and written opinion, PCT/US2015/053992, Jan. 7, 2016, 29 pages.

ScripTalk Station for Patients/En-Vision America—Assistive Technology for the Blond and Low-vision Community; Jul. 17, 2014, http://www.envisionamerica.com/products/scripability/scriptalk/scriptalk-station-for-patients, 7 pages.

\* cited by examiner

MEDICAMENT TRAINING DEVICE AND SYSTEM

BACKGROUND

Performing a medical treatment or test on oneself carries with it certain risks and often creates a level of anxiety for the user performing the treatment or test. It has proven beneficial in the medical field to practice various medical techniques including drug delivery, specifically where it relates to injections and other invasive drug delivery means prior to delivering the medications to a patient in need, and particularly in the case of self-administration of medicaments. Training devices are helpful in reducing errors and anxiety associated with self administering medical treatment, as well as increasing efficiency and accuracy in providing the treatment to patients. Medical devices can be intimidating to use; the fear associated with giving oneself an injection, for example, can be traumatic. This fear is increased in persons with little or no experience in self-administration of medications. Consequently, devices and methods to assist in training individuals to inject themselves or otherwise self-administer medication are beneficial in decreasing or preventing the anxiety associated with medicament delivery. Medicament delivery training devices allow patients to practice giving themselves a full dose in a safe and effective manner.

SUMMARY

In one embodiment, a medicament system configured to communicate information about a medicament device or about a use of a medicament device, or a combination thereof, to a user, is provided. The medicament system may include a medicament device including a housing, and a collateral device, wherein the collateral device may include a collateral device housing comprising an opening for receiving at least a portion of the medicament device, and may further include an adapter configured to interface with and receive a portion of the medicament device. The collateral device may further include an information detecting and/or receiving component configured to receive information from the medicament device and/or a sending component configured to send information to the medicament device, and optionally at least one of: a) a signal output component; b) a microprocessor; c) a storage medium component; and d) a power source, and wherein the medicament device may be configured to generate information detectable by the collateral device, or transmit information to the collateral device, wherein the collateral device may be configured to detect and/or receive information about the medicament device from the medicament device and provide information about the medicament device and/or a feedback about a use of the medicament device to a user of the system. The medicament device may further include a transmitter configured to communicate information and/or signals from the medicament device to the collateral device and/or a remote device, and/or receive information and/or signals from a collateral device and/or a remote device. In non-limiting embodiments, the information detecting/receiving component may include a sensor which may include a microphone, a vibration sensor, or a camera, for example.

In another non-limiting embodiment, a medicament system configured to communicate information about a medicament device or about a use of a medicament device, or a combination thereof, to a user is provided. The medicament system includes a medicament device including a housing, the medicament device including a sensor associated therewith, which in non-limiting examples may include a microphone or a vibration sensor, a transmitter configured to send information from the medicament device, and optionally at least one of: a) a signal output component; b) a microprocessor; c) a storage medium component; and d) a power source, the medicament system including a collateral device, the collateral device including a collateral device housing comprising an opening for receiving at least a portion of the medicament device, and may further include an adapter configured to interface with or receive a portion of the medicament device. The collateral device may further include an information detecting and/or receiving component configured to receive information produced from the sensor and/or a sending component configured to send information to the medicament device, a signal output component, a microprocessor, a storage medium component, and a power source, wherein the collateral device is configured to detect and/or receive information about the medicament device from the medicament device, and/or send information to the medicament device, and/or to provide information about the medicament device and/or a feedback about a use of the medicament device to a user of the system.

In yet another embodiment, a medicament system configured to communicate information about a medicament device or about a use of a medicament device, or a combination thereof, to a user, is provided. The medicament system includes a medicament device having a housing, a collateral device comprising a collateral device housing including an opening for receiving at least a portion of the medicament device, and may further include an adapter configured to interface with and receive a portion of the medicament device. The collateral device may further include a sensor, and an attachment component configured to secure the collateral device to the medicament device. Alternatively, the medicament device may include an attachment component to secure itself to the collateral device. The system may further include, in an embodiment, a sending component configured to send information to the medicament device and/or the collateral device, an information detecting and/or receiving component configured to receive information from the medicament device about the medicament device and/or about a use of the medicament device. The system may further include a signal output component, a microprocessor, a storage medium component, and a power source, wherein the signal output component is configured to provide an output comprising information about the medicament system and/or information about a usage of the medicament device or system to a user of the system.

In another embodiment, a collateral device configured to receive information from and/or detect information about a medicament device is provided. The collateral device includes a collateral device housing, and may further include a detecting and/or a receiving component, wherein the detecting and/or receiving component is configured to detect information about or receive information from the medicament device, a signal output component configured to provide an output to a user, a power source, a microprocessor, and a storage module, wherein the collateral device provides a feedback to a user based on information detected and/or received by the detecting and/or receiving component, in a non-limiting embodiment.

In another embodiment, a method of using a collateral device to train a user of a medicament device to properly operate the medicament device to dispense a dose of medicament and to provide an instruction and/or a feedback to a user of the collateral device is provided. The method may include detecting and/or receiving information from a medicament device, processing information received from the medicament device, and providing a signal output to a user based on information received and processed.

BRIEF DESCRIPTION OF THE DRAWINGS

A more particular description briefly stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which.

DETAILED DESCRIPTION

Figure 1:
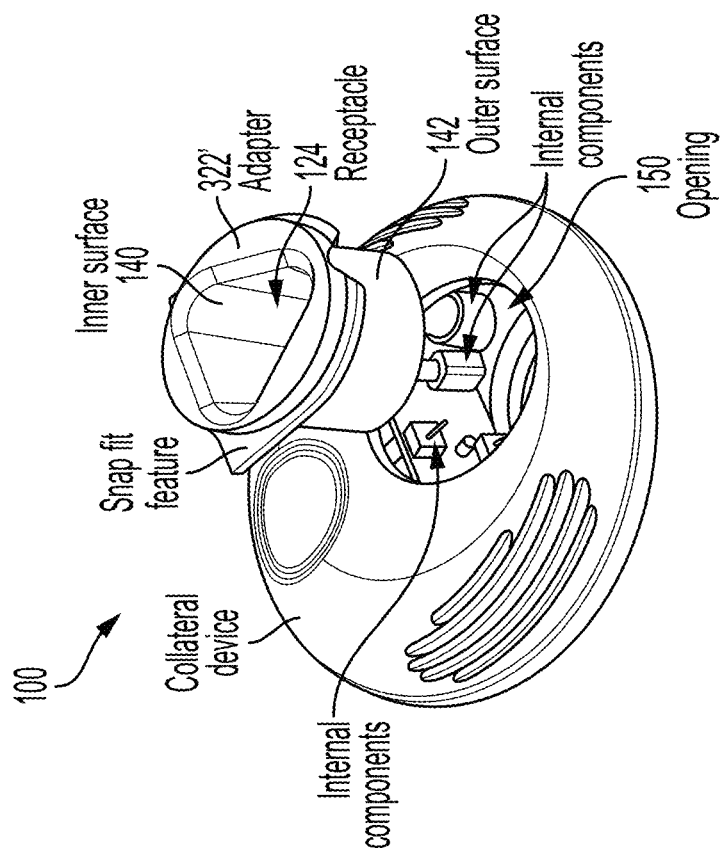
FIG. 1 is a perspective view of a collateral device embodiment comprising a first adapter for receiving a medicament device.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." The modifier "about" used in connection with a quantity is inclusive of the stated value and has the meaning dictated by the context (e.g., includes the degree of error associated with measurement of the particular quantity). It is to be noted that all ranges disclosed within this specification are inclusive and are independently combinable.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order, quantity or importance, but rather the terms first, second, etc., are used to distinguish one element from another.

Embodiments described herein include devices and systems for facilitating accurate medicament delivery or simulation thereof. Further embodiments include devices and systems adapted to receive and deliver In at least one embodiment, there is provided a collateral device for use with one or more medicament devices. The collateral device may include a collateral device housing including a top portion, a bottom portion, and an opening extending there between, the opening configured to receive a portion of the one or more medicament devices, at least a first sensor associated with the collateral device housing for detecting receipt of the portion of one or more medicament devices into the opening, and detecting actuation of an actuation mechanism of the medicament device received therein, an adapter receivable within the opening, the adapter comprising a receptacle for receiving and guiding a portion of a medicament device to a target surface; and a power source. In one embodiment, the first sensor may detect receipt of the portion of the medicament device into the opening and/or the receptacle, and the collateral device may further include at least a second sensor for detecting actuation of an actuation mechanism of the medicament device. In at least one non-limiting embodiment, the first sensor may detect both receipt of the medicament device into the opening and/or the receptacle, and actuation of an actuation mechanism of the medicament device.

In another embodiment, the collateral device may further include at least a third sensor for detecting contact of the bottom portion of the collateral device and/or the medicament device with a target surface.

The sensors described herein include any sensors known in the art, including but not limited to a contact sensor, a light sensor, a proximity sensor, a microphone or a vibration sensor, in non-limiting examples. The collateral device may further include a microprocessor. The collateral device housing may include an internal space created by the housing, wherein internal components of the device may be provided. In some non-limiting embodiments, the internal components may include a microprocessor, sensors, signal output components comprising, for example, speakers, the internal components may further include a timer, or a microphone, for example. The signal output component(s) may provide feedback, guidance and/or training to a user.

The collateral device may be programmed to provide training, guidance, and/or instructions for using the collateral device and/or the medicament device, and/or provide feedback during use of the medicament device and/or collateral device to facilitate training of the user.

In non-limiting embodiments described herein, the collateral device may include an adapter for receiving a medicament device. The adapter may be fixed relative to the collateral device, wherein the adapter may be non-movable relative to the collateral device or may be permanently affixed onto the collateral device. In other embodiments, the adapter may be removable from the collateral device. The adapter(s) may be removable and replaceable relative to the collateral device. The adapters may differ in dimension and/or shape. The adapters may be configured for receiving a particular medicament device and may therefore include a receptacle adapted to receive a particular medicament device having a particular outer shape in its device housing. One collateral device may be useable with a multitude of different medicament devices with different housing profiles whereby the collateral device may include interchangeable adapters comprising receptacles for receiving the medicament device, wherein an inner surface of the adapter may include a profile configured to receive the medicament device housing in a manner to facilitate use of the medicament device relative to the target surface. In at least one example, the inner surface profile of the adapter may be complimentary to the outer housing profile of the medicament device.

In other embodiments, the adapter may be placeable on the medicament device, wherein the adapter and medicament device may be attached to the collateral device for use, and, optionally, removed therefrom following use.

In some non-limiting embodiments, the adapter may be snap fit into the opening of the collateral device as known in the art. Other methods of attaching or affixing the adapter to the collateral device including wherein the adapter includes a first threaded portion on its surface and the opening includes a second threaded portion, wherein the first and second threaded portions interface to retain the adapter onto the collateral device.

In at least one further non-limiting embodiment, the collateral device may include or may be adapted to function in conjunction with a Smartphone, wherein the Smartphone is configured to receive information from the collateral device and/or the medicament device, send information to the collateral device and/or the medicament device, provide feedback to a user, and/or provide feedback to the collateral device and/or the medicament device. In one example, a Smartphone may be configured to include a collateral device adapter, wherein the collateral device adaptor includes the housing having the opening and, optionally, the adapter having the receptacle for receiving the medicament device. In other embodiments, a Smartphone may be used to interface with the collateral device embodiments described otherwise herein by receiving and/or communicating information to/from the collateral device and/or the medicament device and/or a remote location. In some embodiments the collateral device may include an attachment device for attaching or affixing, removably, the collateral device to a medicament device, to a user, or both. In some examples, the collateral device may be affixed or attached to a user with an adhesive on its bottom portion surface. In other embodiments, hook and loop attachment member may be placed on the collateral device and a mating hook/loop member may be placed on a target surface to affix the collateral device to the target surface. Other attachment devices for affixing the collateral device to a target surface known in the art may also be used, including, but not limited to a clip member.

The sensors described herein may provide the ability to detect proper receipt of the medicament device within the collateral device and/or within the adapter. Moreover, the sensors may detect correct placement of the collateral device on the target surface, and a combination of correct seating of the medicament device in the collateral device and placement of collateral device on target surface, in one non-limiting embodiment. In another example, the sensors may detect whether the collateral device is removed from the target surface and/or the medicament device is removed from the collateral device and/or the target surface after initiation of a drug delivery (after actuation) and prior to completion of an injection, for example (i.e., a wet injection). Feedback may be provided to a user as a result, and/or the injection may be halted as a result, in non-limiting examples.

Figure 2:
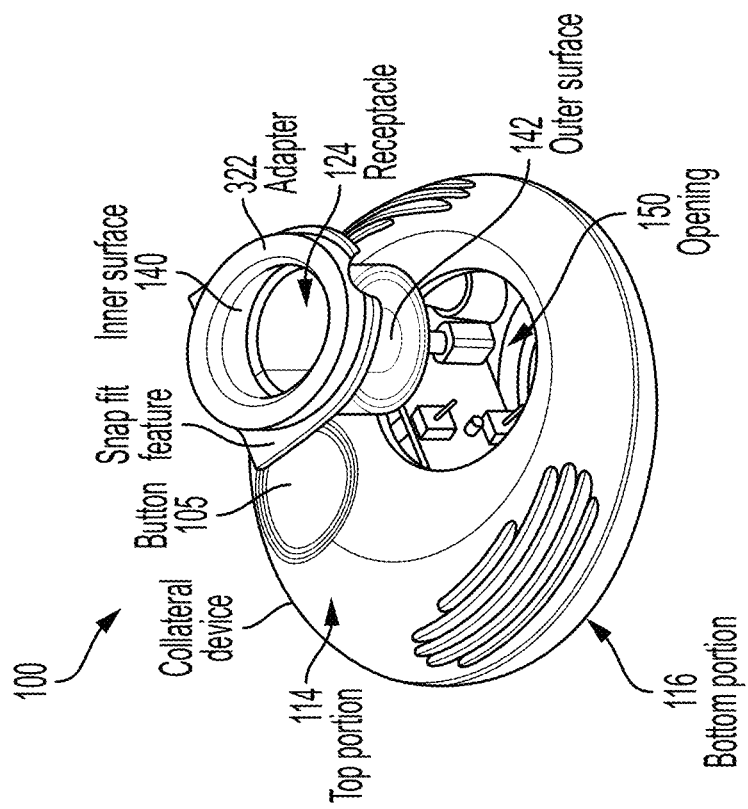
FIG. 2 is a perspective view of the collateral device embodiment comprising a second adapter for receiving a medicament device.

FIGS. 1-2 provide a non-limiting embodiment of a collateral device 100, including a housing having a top portion 114 and a bottom portion 116, an defining an opening 150 there between. An adapter 322, 322' is receivable within the opening 150 of the collateral device. The adapter includes an inner surface 140 and an outer surface 142, the inner surface 140 defining a receptacle 124 for receiving a medicament device, in one embodiment. The inner surface 140 of the collateral device 100 may include a profile configured to receive an outer housing profile of a particular medicament device. For example, as seen in FIGS. 1-2, the collateral device 100 may receive different adapters 322, 322', for receiving different medicament devices. These adapters 322, 322' may only differ by an inner surface 140 profile that corresponds to, and in some instances, is complementary to a medicament device outer housing such that the medicament device may be received within the receptacle 124, and is thereby guided to the target surface. In some examples, the adapter 322, 322' may be snap fit by way of a snap fit feature into the opening 150 of the collateral device such that the adapters 322, 322' are easily removable, replaceable, and exchangeable relative to the collateral device 100, in some embodiments. The internal components of the collateral device are shown in FIGS. 1-2, which may include sensors, microphone, speakers, microprocessor, timers, and the like. A multifunction button 105 may be included to either power on/off the device, and/or release the adapter 322, 322' from the collateral device, and/or release the medicament device from the collateral device 100 in non-limiting examples.

Figure 5:
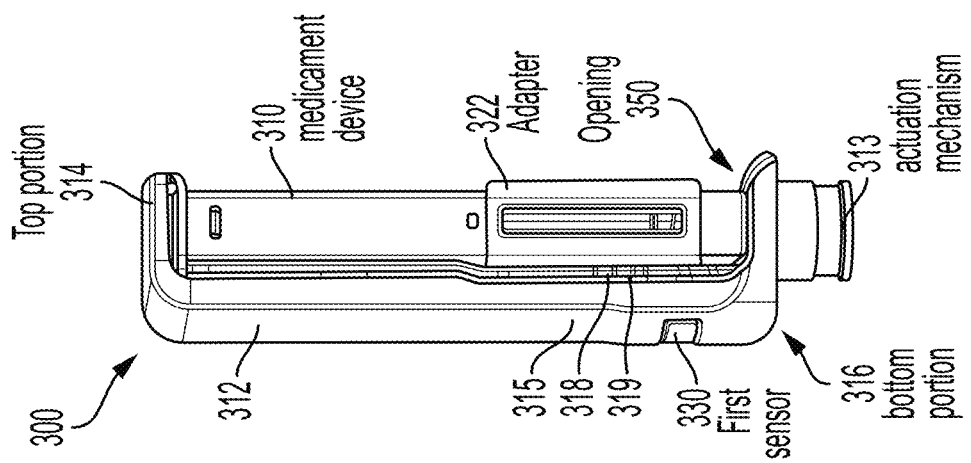
FIG. 5 is a side view of a medicament system having a collateral device and a medicament device.
Figure 4:
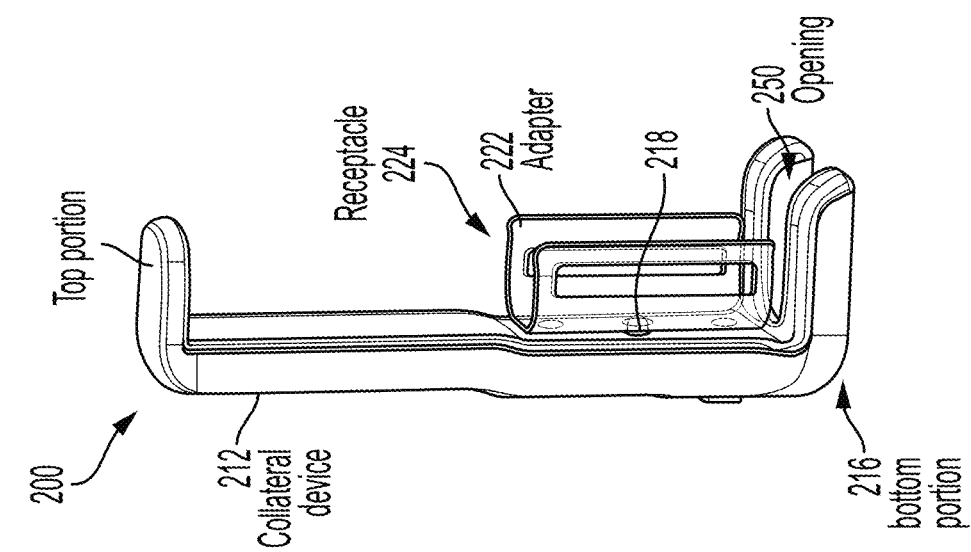
FIG. 4 is a side view of the collateral device of FIG. 3, comprising another adapter for receiving a medicament device.
Figure 3:
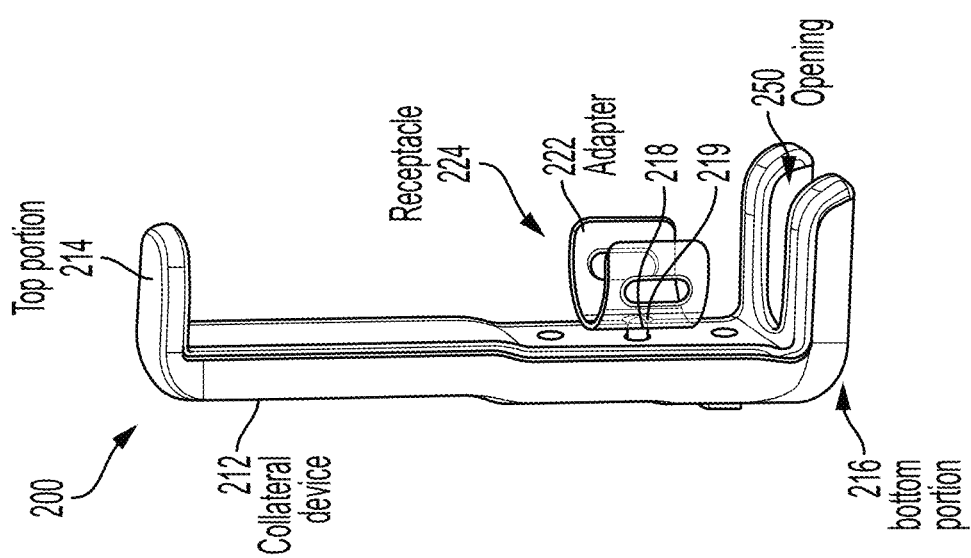
FIG. 3 is a side view of a further embodiment of a collateral device comprising an adapter for receiving a medicament device.

In some non-limiting embodiments, a medicament system 300 as shown in FIG. 5, configured to receive and/or communicate information about the system 300, about a medicament device 310 or about a use of the medicament device 310, a collateral device, 312 or a combination thereof, to a user, said medicament system 300 including a medicament device 310 comprising a housing comprising an actuation mechanism 313. In some embodiments the medicament device 310 may be button actuated or shield actuated. The system 300 may further include a collateral device 312 comprising a collateral device housing having a top portion 314, a bottom portion 316, said collateral device 312 housing defining an opening 350 for receiving a portion of the medicament device 310, and an adapter 322 comprising a receptacle 324 (not visible in FIG. 5) for receiving a portion of the medicament device 310 being positionable within the opening 350. The system 300 may further include at least a first sensor 330 associated with the collateral device housing for detecting receipt of the portion of the medicament device 310 into the opening 350, and optionally, or in addition, a second sensor 332 which may be associated with the collateral device housing for detecting actuation of the actuation mechanism. The first sensor 330, may optionally detect actuation of the actuation mechanism 313, removing the need for a second sensor 332, in one non-limiting embodiment. However, in an alternative embodiment, the system 300 may include both a first and a second sensor 330, 332. The second sensor 332 may include a microphone or vibration sensor, in non-limiting examples. The system may further include a microprocessor; and a power source (not shown in FIG. 5). In some non-limiting embodiments of the system 300 as described otherwise related to embodiments of the collateral device described herein, the adapter 322 may be removable from the collateral device 312. It may be configured to snap fit within the opening of the collateral device as describe related to FIGS. 1-2, or alternatively, it may be attachable onto (and removable from) a portion of the collateral device housing 315 as shown in FIGS. 3-5.

Example methods of attachment for the adapter 322 are described herein, including a first threaded portion, and wherein the collateral device housing includes a second threaded portion, such that the first and second threaded portions interface with one another when the adapter is placed within onto the device to retain the adapter. In other examples as show in FIGS. 3-5, the collateral device housing 215, 315 may include a protrusion 218, 318, and the adapter 222, 322 may include a notch or an aperture 219, 319 for attaching the adapter to the collateral device housing 215, 315, for example. The protrusion may alternatively be formed on the adapter, and the notch or aperture on the collateral device, in a non-limiting example. The adapter 222, 322 may include an outer surface and an inner surface, said inner surface defining the receptacle 224, 324 for receiving the medicament device 310.

As described herein, the inner surface of the adapter may include a profile complimentary to an outer surface of a medicament device 310 housing. The system 300 may further include a signal output component to provide a feedback, training and/or guidance to a user. In other non-limiting embodiments the system may include a Smartphone in communication with the system, and its components, or in place of the collateral device, for example. The Smartphone configured to receive information from the collateral device, send information to the collateral device, provide feedback to a user, and/or provide feedback to the collateral device.

As otherwise described herein, the system 300 may include one or more attachment devices for removably affixing the collateral device 312 to a medicament device 310 or the medicament device 310 to the collateral device 312, or either one of the collateral or medicament device to a user, or a combination thereof. The medicament device described herein may include a drug delivery device or a medicament simulation device used for training, or a combination drug delivery and training/simulation device.

In another non-limiting embodiment, a method for delivering medicament or simulating medicament delivery to a user is provided, including, a collateral device comprising a collateral device housing comprising a top portion, a bottom portion, said collateral device housing defining an opening configured to receive an adapter, and an adapter positionable within the opening, including a receptacle for receiving a portion of the medicament device to deliver the medicament device to a target surface, further comprising, a medicament device comprising a housing including an actuation mechanism, wherein at least a portion of the medicament device is placed within the receptacle prior to: 1) placement of the adapter into the opening of the collateral device and subsequent actuation of the medicament device; or 2) actuation of the medicament device, wherein the collateral device and/or the adapter comprises at least one sensor for detecting receipt of a portion of the medicament device and/or actuation of the medicament device and provides feedback to a user based thereon. Wherein when the medicament device is placed within the receptacle according to (2) prior to actuation of the medicament device, the adapter is positioned onto the collateral device before the medicament device is placed with in the receptacle and prior to actuation of the medicament device, in at least one non-limiting embodiment.

What is claimed is:

1. A collateral device for use with one or more medicament devices, the collateral device comprising:
    a collateral device housing comprising a top portion, a bottom portion, and an opening extending there between;
    at least a first sensor associated with the collateral device housing for detecting receipt of the portion of one or more medicament devices into the opening, and detecting actuation of an actuation mechanism of the medicament device, said medicament device comprising a housing, and an actuation mechanism;
    an adapter receivable within the opening, the adapter comprising a receptacle for receiving the medicament device wherein the collateral device is configured to detect receipt or removal of the medicament device, and guide a portion of the medicament device to a target surface; and
    a power source.

2. The collateral device of claim 1, wherein the first sensor detects receipt of the portion of the medicament device into the opening, and wherein the collateral device further comprises at least a second sensor for detecting actuation of the actuation mechanism of the medicament device.

3. The collateral device of claim 1, further comprising at least a third sensor for detecting contact of the bottom portion of the collateral device and/or of the medicament device received therewithin with the target surface.

4. The collateral device of claim 1, wherein the first sensor comprises a contact sensor, a light sensor, a proximity sensor, a microphone or a vibration sensor.

5. The collateral device of claim 1, further comprising a microprocessor.

6. The collateral device of claim 5, wherein the collateral device is programmed to provide training, guidance, and/or instructions for using the collateral device and/or the medicament device.

7. The collateral device of claim 1, wherein the adapter is removable from the collateral device housing.

8. The collateral device of claim 7, wherein the adapter comprises a first threaded portion, and wherein the collateral device housing surrounding the opening comprises a second threaded portion, such that the first and second threaded portions interface with one another when the adapter is placed within the opening to retain the adapter within the opening.

9. The collateral device of claim 1, wherein the adapter comprises an outer surface and an inner surface, said inner surface defining the receptacle for receiving the medicament device.

10. The collateral device of claim 1, further comprising a signal output component to provide a feedback, training and/or guidance to a user.

11. The collateral device of claim 1, further comprising a Smartphone configured to receive information from the collateral device, send information to the collateral device, provide feedback to a user, and/or provide feedback to the collateral device.

12. The collateral device of claim 1, further comprising one or more attachment devices for removably affixing the collateral device to the medicament device, to a user, or both.

13. A medicament system configured to receive and/or communicate information about the system, about a medicament device or about a use of the medicament device, or a combination thereof, to a user, said medicament system comprising:
    a medicament device comprising a housing comprising an actuation mechanism;

a collateral device comprising a collateral device housing comprising a top portion, a bottom portion, said collateral device housing defining an opening configured to receive a portion of the medicament device, and an adapter comprising a receptacle for receiving a portion of the medicament device being positionable within the opening;

at least a first sensor associated with the collateral device housing for detecting receipt of the portion of the medicament device into the opening;

at least a second sensor associated with the collateral device housing for detecting actuation of the actuation mechanism;

a microprocessor; and a power source.

14. The medicament system of claim 13, wherein the adapter is removable from the collateral device housing.

15. The medicament system of claim 14, wherein the adapter is configured to snap fit within the opening of the collateral device housing.

16. The medicament system of claim 14, wherein the adapter comprises a first threaded portion, and wherein the collateral device housing surrounding the opening comprises a second threaded portion, such that the first and second threaded portions interface with one another when the adapter is placed within the opening to retain the adapter within the opening.

17. The medicament system of claim 13, wherein the adapter comprises an outer surface and an inner surface, said inner surface defining the receptacle for receiving the medicament device.

18. The medicament system of claim 17, wherein the inner surface comprises a profile complimentary to an outer surface of a medicament device housing.

19. The medicament system of claim 13, further comprising a signal output component to provide a feedback, training and/or guidance to a user.

20. The medicament system of claim 13, further comprising a Smartphone configured to receive information from the collateral device, send information to the collateral device, provide feedback to a user, and/or provide feedback to the collateral device.

21. The medicament system of claim 13, further comprising one or more attachment devices for removably affixing the collateral device to the medicament device or the medicament device to the collateral device, or either one of the collateral or medicament device to a user, or a combination thereof.

* * * * *